United States Patent [19]

Sugawara et al.

[11] Patent Number: 4,470,832
[45] Date of Patent: Sep. 11, 1984

[54] GAS CHROMATOGRAPHIC APPARATUS

[75] Inventors: Katuo Sugawara, Hitachi; Ictitaro Tani, Kitaibaraki; Hideo Tsukioka, Mito; Etsuo Ohe; Etsunori Mori, both of Hitachi, all of Japan

[73] Assignee: Hitachi, Ltd., Tokyo, Japan

[21] Appl. No.: 473,815

[22] Filed: Mar. 9, 1983

[30] Foreign Application Priority Data

Mar. 10, 1982 [JP] Japan .................................. 57-36483
Apr. 26, 1982 [JP] Japan .................................. 57-68701

[51] Int. Cl.³ .............................................. B01D 15/08
[52] U.S. Cl. ........................................ 55/197; 55/386
[58] Field of Search ................. 55/197, 386; 210/659, 210/198.2

[56] References Cited

U.S. PATENT DOCUMENTS

| | | | |
|---|---|---|---|
| 3,373,872 | 3/1968 | Hrdina | 55/386 |
| 4,137,161 | 1/1979 | Shimada | 210/659 |
| 4,274,967 | 1/1981 | Snyder | 55/386 |

FOREIGN PATENT DOCUMENTS

162049 2/1981 Japan .

*Primary Examiner*—John Adee
*Attorney, Agent, or Firm*—Antonelli, Terry & Wands

[57] ABSTRACT

A gas chromatographic apparatus having at least two gas separation columns arranged in parallel to each other, the outlet of the first gas separation column being connected to a gas sensor through a column switch valve, and the outlet of the second gas separation column being connected to the column switch valve through a gas detection time-controlling pipe, where when the first gas separation column is communicated with the gas sensor, the outlet of the second gas separation column is made open to the atmosphere by the column switch valve, or when the second gas separation column is communicated with the gas sensor, the outlet of the first gas separation column is made open to the atmosphere by the column switch valve, or the apparatus having a first gas separation column whose inlet is connected to the switch valve and at least two second columns whose inlets are connected to the outlet of the first gas separation column, whose outlets are connected to the gas sensor and which are arranged in parallel to each other through the column switch valve, where the first gas separation column, one of the second columns and the column switch valve are communicated with each other, by the column switch valve. A chromatogram with distinctly separated peaks in a continued state can be obtained in a short time by only one detecting and recording means.

16 Claims, 6 Drawing Figures

GAS CHROMATOGRAPHIC APPARATUS

BACKGROUND OF THE INVENTION

This invention relates to a gas chromatographic apparatus, and more particularly to a gas chromatographic apparatus with a gas calibration tube, a gas separation column, a gas sensor, etc.

When various gas components were detected through one detecting operation, for example, when gas concentrations of six gas components, e.g. $H_2$, CO, $CH_4$, $C_2H_2$, $C_2H_4$ and $C_2H_6$, in a gas permeated through a polymeric membrane and stored in a gas calibration tube were measured in one gas separation column by gas chromatographic separation and quantitative determination, a very long gas separation column was needed with a very long detection time. To this end, a programmed temperature gas chromatography was needed. However, in the case of measurement where no such programmed temperature gas chromatography was available, a gas chromatographic apparatus as shown in FIG. 1 was needed for measurement. That is, a gas mixture consisting of, for example, 6 components, A, B, C, D, E and F stored in a gas calibration tube 1 through a valve 2 is introduced into gas separation columns 5a and 5b arranged in parallel with each other together with a carrier gas from a carrier gas source 4 through a switch valve 3, for example, a 6-way valve. The gas components separated in the gas separation columns 5a and 5b are introduced into gas sensors 6a and 6b, respectively, and their detections are amplified in amplifiers 7a and 7b and recorded in recorders 8a and 8b, respectively. In FIG. 1, numerals 9a and 9b are different gas separation fillers, i.e. different adsorbents with different adsorbabilities, filled in the gas separation columns, 5a and 5b, respectively. Numeral 10 is a gas flow rate controller. When gas sensors 6a and 6b are provided for two gas separation columns 5a and 5b suitable for gas separation, respectively, in this manner, 6 components A-F can be separated and measured, and the so-called chromatograph as shown in FIG. 2 can be obtained on recording papers on recorders 8a and 8b when the detections by gas sensors 6a and 6b are recorded on the recorders 8a and 8b. That is, the chromatogram shows outputs from gas sensors 6a and 6b on the axis of ordinate and time on the axis of abscissa, and the results of separation and detection in one system of gas separation column 5a, gas sensor 6a, amplifier 7a and recorder 8a are shown by full line in FIG. 2, where, among 6 components, components A, B and C are distinctly separated and detected, whereas components D, E and F are not distinctly separated and detected. On the other hand, the results of separation and detection in another system of gas separator column 5b, gas sensor 6b and amplifier 7b and recorder 8b are shown by dotted line in FIG. 2, where, among 6 components, components A, B and C are not distinctly separated and detected, whereas components D, E and F are distinctly separated and detected. In a chromatogram the time up to a peak appearance is called "retention time" of a component, and utilized for qualitative determination of the component, and an area or height of the peak is utilized for quantitative determination of the component.

In the gas chromatographic apparatus shown in FIG. 1, components A-F can be separated and detected, but the chromatograms are obtained from each of the system of gas separation column 5a, and gas sensor 6a and the system of gas separation column 5b and gas sensor 6b, and thus the results cannot be obtained on one chromatogram in a continued state. Thus, connection of the two recorders to a data processing unit for calculating concentrations of gas components from the chromatograms, is a troublesome labor, resulting in complicated operation. In this case, two interfaces to the data processing unit are required for the gas sensors 6a and 6b, and this is quite uneconomical.

SUMMARY OF THE INVENTION

An object of the present invention is to provide a gas chromatographic apparatus for producing a chromatogram in a continued state in a short time.

According to a first aspect of the present invention, a gas chromatographic apparatus is provided, which comprises a gas calibration tube, a gas separation column connected to the gas calibration tube through a switch valve of switching a carrier gas passage, and a gas sensor connected to the gas separation column and destined to detect separated gas components, wherein the gas separation column comprises at least two gas separation columns, arranged in parallel to each other, the outlet of the first gas separation column is connected to the gas sensor through a column switch valve, the outlet of the second gas separation column is connected to the column switch valve through a gas detection time-controlling pipe, and when the first gas separation column is communicated with the gas sensor, the outlet of the other gas separation column is made open to the atmosphere by the column switch valve, whereas when the second gas separation column is communicated with the gas sensor, the outlet of the first gas separation column is made open to the atmosphere by the column switch valve, and preferably the gas detection time-controlling pipe has an inner diameter of not more than 4 mm, the column switch valve is a 4-way electromagnetic valve, and more preferably the 4-way electromagnetic valve is actuated a definite time after a gas in the gas calibration tube is made to flow into the gas separation columns.

According to a second aspect of the present invention, a gas chromatographic apparatus is provided, which comprises a gas calibration tube, a gas separation column connected to the gas calibration tube through a switch valve of switching a carrier gas passage, and a gas sensor connected to the gas separation column and destined to detect separated gas components, wherein the gas separation column comprises a first gas separation column whose inlet is connected to the switch valve, and at least two second columns whose inlets are connected to the outlet of the first gas separation column, whose outlets are connected to the gas sensor, and which are arranged in parallel to each other through a column switch valve, and the first gas separation column, one of the second columns and the gas sensor are communicated with one another by the column switch valve, and preferably the second columns arranged in parallel have an identical length, an identical inner diameter and fillers of identical particle size therein, and the column switch valve is a 3-way electromagnetic valve.

The present invention will be described in detail below, referring to the accompanying drawings.

PREFERRED EMBODIMENTS OF THE INVENTION

Figure 1:
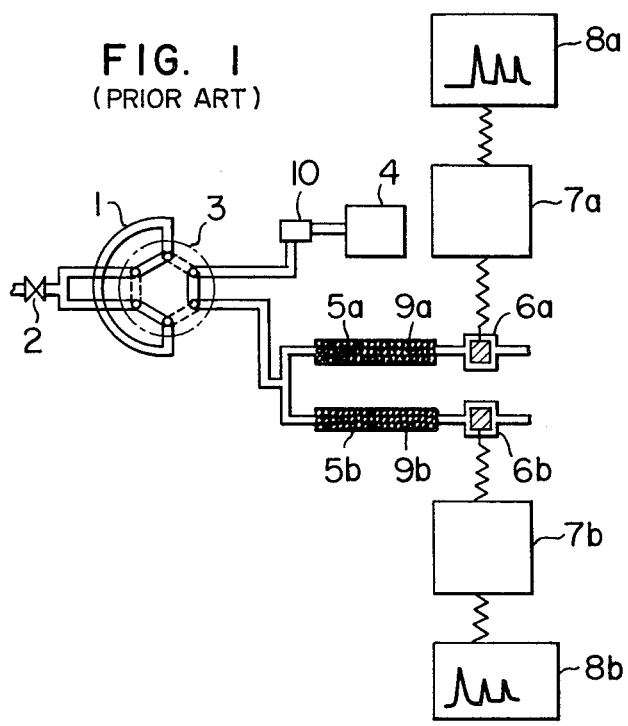
FIG. 1 is a schematic flow diagram of a gas chromatographic apparatus so far proposed.
Figure 3:
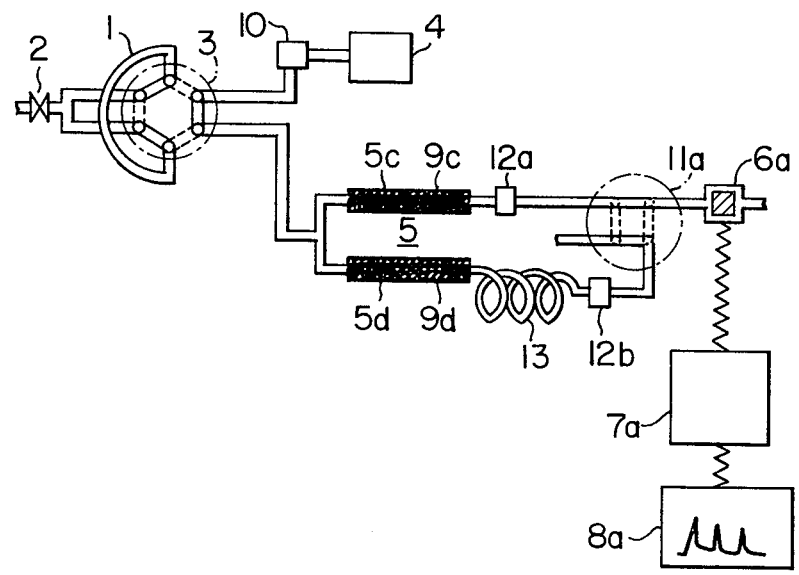
FIG. 3 is a schematic flow diagram of one embodiment of the gas chromatographic apparatus according to the present invention.

In FIG. 3, an embodiment of the present invention according to a first aspect of the present invention is shown, where the same members as shown in FIG. 1 are identified with the same numerals and their explanation will be thus omitted. In the present embodiment, two gas separation columns are provided in parallel to each other. That is, a first gas separation column 5c whose inlet is connected to a 6-way switch valve 3, and a second gas separation column 5d whose inlet is connected to the 6-way switch valve 3 and which is arranged in parallel to the first gas separation column 5c are provided. The outlet of the first gas separation column 5c is connected to a gas sensor 6a through a column switch valve 11, for example, a 4-way switch valve, and the outlet of the second gas separation column 5d is connected to the gas sensor 6a through the column switch valve 11 and a gas detection time-controlling pipe 13. When the first gas separation column 5c is communicated with the gas sensor 6a by the column switch valve 11, the outlet of the second gas separation column 5d is made open to the atmosphere, whereas when the second gas separation column 5d is communicated with the gas sensor 6a by the column switch valve 11, the outlet of the first gas separation column 5c is made open to the atmosphere. By this arrangement, the gas components not separated in the second gas separation column 5d are vented to the atmosphere without passing to the gas sensor 6a while the gas components are separated in the first gas separation column 5c and detected by the gas sensor 6a, and the gas components separated in the second gas separation column 5d are made to remain in the gas detection time-controlling pipe 13 until the gas components separated in the first gas separation column 5c has been detected and measured by the gas sensor 6a. After the completion to detect and measure the gas components separated in the first gas separation column 5c, the gas components separated in the second gas separation column 5d and made to remain in the gas detection time-controlling pipe 13 can be detected and measured by the gas sensor 6a, whereby a chromatogram of various gas components in a continued state can be obtained in a short time. While the gas components separated in the second gas separation column 5d is detected and measured by the gas sensor 6a, the gas passing through the first gas separation column 5c is vented to the atmosphere through the column switch valve 11.

Figure 4:
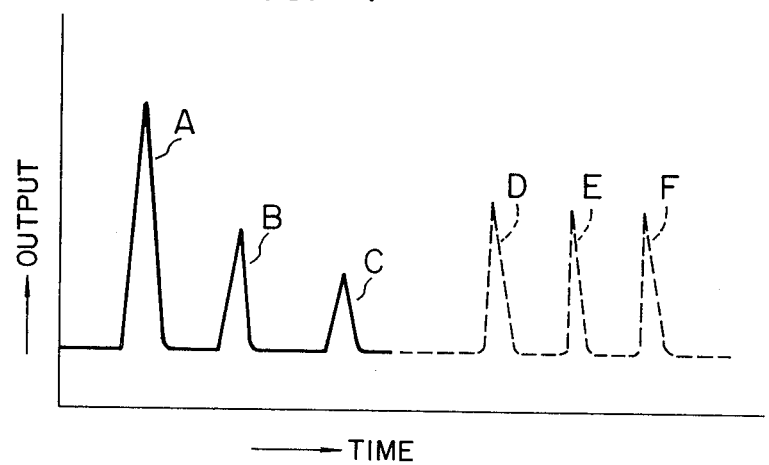
FIG. 4 is a chromatogram of 6 gas components obtained by the gas chromatographic apparatus of FIG. 3.

That is, the column switch valve 11 is set to the state shown by full line in FIG. 3, and the 6-way switch valve 3 is switched to the passages shown by dotted lines in FIG. 3 to pass a mixed gas of 6 components A, B, C, D, E, and F through the first gas separation column 5c, so that the gas components can be measured by the gas sensor 6a, whereby a chromatogram of components A, B and C shown by full line in FIG. 4 can be obtained. After the completion to detect the gas components A, B and C, the column switch valve 11 is switched to the state shown by dotted lines in FIG. 3 to separate gas components in the second gas separation column 5d and make the separated gas components remain in the gas detection time-controlling pipe 13, and then the components, for example, D, E and F thus delayed in discharge are detected and measured by the gas sensor 6a, whereby a chromatogram of gas components D, E and F as shown by dotted line in FIG. 4 can be obtained as continued to the chromatogram of components A, B and C.

In FIG. 3, 9c and 9d show gas separation fillers and 12a, 12b and 12c are carrier gas flow rate controllers.

In this manner, many gas components can be detected and measured by only one gas sensor in this embodiment, and the unwanted peaks are not overlapped with the effective peaks in the chromatogram. Furthermore, only one interface to a data processing unit is needed for calculating gas concentrations, etc. from the outputs from the gas sensor 6a.

When there is no substantially large time difference between the components C and D in FIG. 3, a longer gas detection time-controlling pipe 13 must be used. The gas detection time-controlling pipe 13, as provided just before the inlet of the second gas separation column 5d, can have the same effect as provided just after the outlet of the second gas separation column 5d. That is, it can be provided not only after the outlet as shown in FIG. 3 but also before the inlet of the second gas separation column 5d.

When the inner diameter of the gas detection time-controlling pipe 13 is increased, the peaks on the chromatogram become broader, and thus the inner diameter of the pipe 13 is desirably not more than 4 mm.

The column switch valve 11 can be a 4-way electromagnetic valve and can be interlocked with the 6-way switch valve 3. Thus, the column switch valve 11 is not always limited to manual operation.

According to the first aspect of the present invention, as described above, a first gas separation column and a second gas column with a gas detection time-controlling pipe are provided in parallel to each other. Where the gas components separated in the second gas separation column can be detected and measured successively after the completion to detect and measure the gas components separated in the first gas separation column, and a chromatogram of various gas components as distinct peaks in a continued state can be obtained in a short time.

Figure 5:
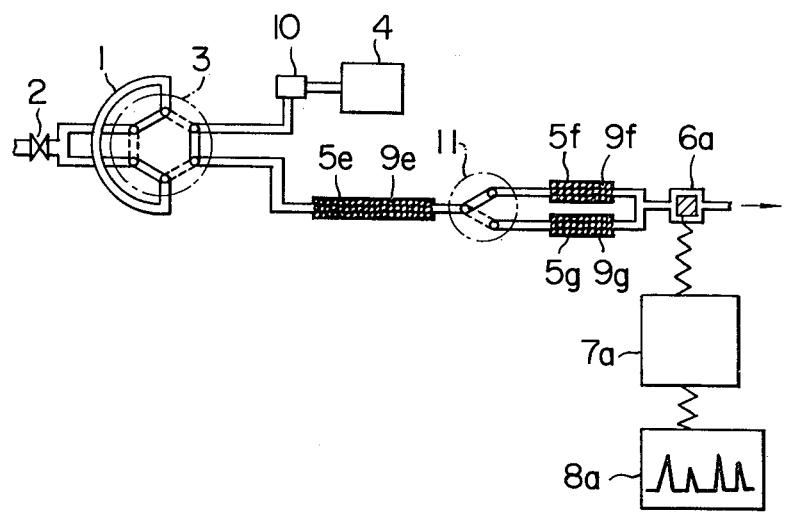
FIG. 5 is a schematic flow diagram of another embodiment of the gas chromatographic apparatus according to the present invention.

In FIG. 5, another embodiment according to the second aspect of the present invention is shown, where the same members as in FIGS. 1 and 3 are identified with the same numerals, and their explanation will be thus omitted. In the present embodiment, a first gas separation column 5e, whose inlet is connected to a switch valve 3 and at least two second columns 5f and 5g whose inlets are connected to the outlet of the first gas separation column 5e, whose outlets are connected to a gas sensor 6a, and which are arranged in parallel to each other through a column switch valve 11, are provided, where the first gas separation column 5e, one of the second column 5f and the gas sensor 6a, or the first gas separation column, the other second column 5g and the gas sensor 6a are communicated with one another by the column switch valve 11. The column switch valve 11 can be, for example, a 3-way switch valve, and is provided between the outlet of the first gas separation column 5e and the inlets of the second columns 5f and 5g. One of the second column 5f serves as a gas separation column, and the other second column 5g serves as a pressure and flow rate-controlling means and is principally not directed to gas separation. With this arrangement, a chromatogram of distinct peaks in a continued state can obtained in a short time. For example, a mixed gas consisting of 6 components A-F is introduced into a gas calibration tube, and then a 6-way switch valve 3 is switched to the state shown by dotted lines in FIG. 5, whereby a carrier gas from a carrier gas source 4 pushes the mixed gas of 6 components in the gas calibration tube 1 to a gas sensor 6a through the first gas separation column 5e and one of the second column 5f, where the 6-way switch valve 3 and the 3-way column switch valve 11 are usually in the state shown by full lines in FIG. 5, and the carrier gas from the carrier gas source 4 can contact the gas sensor 6a through the first gas separation column 5e and one of the second columns 5f. With this arrangement, a chromatogram with distinct peaks of gas components A, B and C shown and less distinct peaks of gas components D, E and F as shown by full line in FIG. 2 can be obtained on a recorder 8a through an amplifier 7a, because species of gas separation fillers 9e and 9f in the first gas separation column 5e and the second column 5f, respectively, the lengths of both columns 5e and 5f, etc. are so selected in advance as to obtain such a chromatogram.

Figure 2:
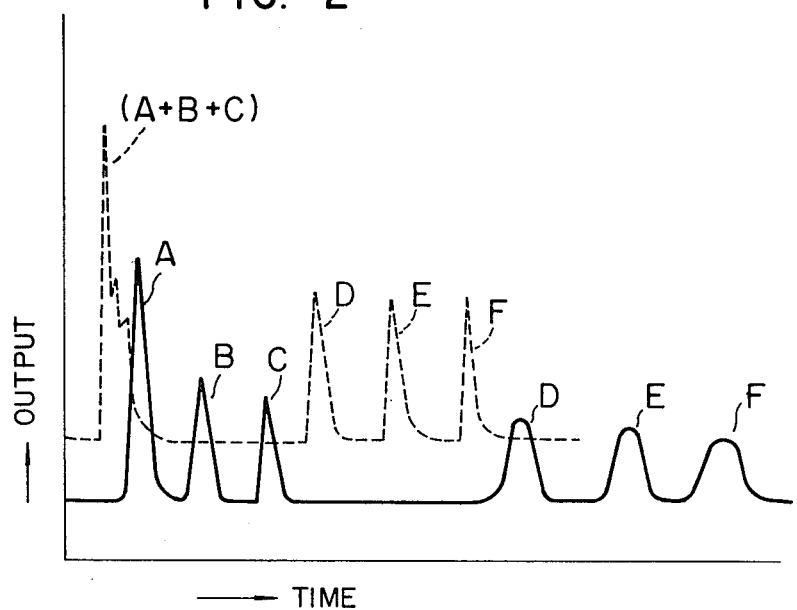
FIG. 2 is chromatograms of 6 gas components obtained by the gas chromatographic apparatus of FIG. 1.

Then, the 3-way column switch valve 11 is switched to the state shown by dotted lines in FIG. 5 to introduce the mixed gas to the gas sensor 6a through the first gas separation column 5e and the other second column 5g, whereby a chromatogram with distinct peaks of gas components D, E and F and less distinct peaks of gas components A, B and C as shown by dotted line in FIG. 2 can be obtained on the recorder 8a through the amplifier 7a, because the species of pressure or flow rate-controlling filler 9g in the other second column 5g, the length of column 5g, etc. are so selected in advance as to obtain such a chromatogram.

That is, the first gas separation column 5e is common to the second columns 5f and 5g, and the first gas separation column 5e is directed to separation of gas components D, E and F of 6 components A-F, and not to separation of gas components A, B and C, and one of the second columns 5f is directed to separation of gas components A, B and C, and the other second column 5g is directed only to pressure or flow rate controlling to provide the same pressure or flow rate condition as in the second column 5f, and only when required, for example, when the gas components D, E and F are not throughly separated in the first gas separation column 5e, the second column 5g can be used as an auxiliary gas separation column. Thus, the second column 5g usually taking as part in separation of gas components D, E and F has the same inner diameter and length as those of the second column 5f and also fillers of no gas separability having the same particle size as that of the fillers for the second column 5f.

To obtain a chromatogram of distinct peaks of gas components A-F in a continued state, the 3-way column switch valve 11 is set to the state shown by full lines in FIG. 5 to detect components A, B and C separated in the second column 5f, and then the 3-way column switch valve 11 is switched to the state shown by dotted lines in FIG. 5 to detect gas components D, E and F separated in the first gas separation column 5e. With this arrangement, a chromatogram with distinct peaks of gas components A, B and C as shown by full line in FIG. 4 and distinct peak of gas components D, E and F as shown by dotted line in FIG. 4 can be obtained with time, but the height of peaks twice that of those of FIG. 4 can be obtained in the apparatus of FIG. 5, because of twice the output from the apparatus of FIG. 3 owing to the series connection of the columns in FIG. 5 and not to the parallel connection of the columns in FIG. 3.

Thus, distinct peaks of 6 gas components can be detected only by one gas sensor 6a as in FIG. 3, in contrast to two in the so far proposed chromatographic apparatus, and accordingly, only one interface connected to a data processing unit is necessary for calculating gas concentrations from the outputs from the gas sensor 6a. As described above, the mixed gas is supplied to the first gas separation column 5e and the second column 5f or 5g by switching the column switch valve 11 without dividing the mixed gas into two portions as in FIG. 1 or 3, and the output recording on the chromatogram is enhanced.

The column switch valve 11 can be a 3-way electromagnetic valve and interlocked with the 6-way switch valve. The 3-way electromagnetic valve 11 can be interlocked with the completion to detect the gas components A, B and C to simplify the operation.

When the second columns 5f and 5g have different lengths and the 3-way column switch valve 11 is switched, the flow rates of carrier gas will be changed and the so-called base line, i.e. the axis of abscissa on the chromatogram will be changed to lower the accuracy of quantitative determination, and thus the inner diameter and length of the second columns 5f and 5g and the particle size of fillers 9f and 9g must be the same therebetween. With this arrangement, there is no need for adjusting the flow rate of carrier gas.

It is necessary to provide some time difference in separation and detection between gas components C and D as shown in FIG. 4 for switching operation of column switch valve 11, and if it is impossible to do so on account of gas separation property, a detection time-controlling pipe as in the first aspect of the present invention can be provided between the column switch valve 11 and the second column 5g to provide the necessary detection time difference.

Various commercially available fillers can be used for fillers 9e, 9f and 9g, and the optimum fillers can be selected therefrom upon necessity. For each of columns 5e and 5f, a plurality of gas separation fillers can be used to optimum gas separation, and thus each column is not limited to only one species of gas separation filler.

Figure 6:
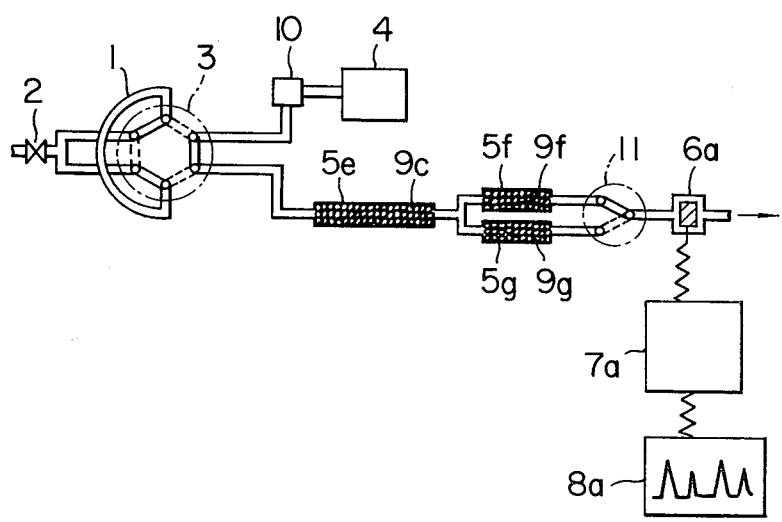
FIG. 6 is a schematic flow diagram of another embodiment of the gas chromatographic apparatus according to the present invention.

In FIG. 6, a further embodiment of the present invention is shown, where the 3-way column switch valve 11 is provided at the outlets of the second columns 5f and 5g and the same function and effect as in FIG. 5 can be obtained.

According to the second aspect of the present invention, as described above, the first gas separation column, one of the second columns and the gas sensor are communicated with one another by the column switch valve, and various gas components can be separated and detected continuously by switching the column switch valve, and a chromatogram with distinct peaks of gas components in a continued state can be obtained in a short time.

What is claimed is:

1. A gas chromatographic apparatus which comprises a gas calibration tube, a gas separation column connected to the gas calibration tube through a switch valve of switching a carrier gas passage, and a gas sensor connected to the gas separation column and destined to detect separated gas components, the gas separation column comprising at least two gas separation columns arranged in parallel to each other, the outlet of the first gas separation column being connected to the gas sensor through a column switch valve, and the outlet of the second gas separation column being connected to the column switch valve through a gas detection time-controlling pipe, where when the first gas separation column is communicated with the gas sensor, the outlet of the second gas separation column is made open to the atmosphere by the column switch valve, whereas when the second gas separation column is communicated with the gas sensor, the outlet of the first gas separation column is communicated with the gas sensor, the outlet of the first gas separation column is made open to the atmosphere by the column switch valve.

2. The gas chromatographic apparatus according to claim 1, wherein the gas detection time-controlling pipe has an inner diameter of not more than 4 mm.

3. The gas chromatographic apparatus according to claim 1, wherein the column switch valve is a 4-way electromagnetic valve.

4. The gas chromatographic apparatus according to claim 3, wherein the 4-way electromagnetic valve is actuated a definite time after a gas in the gas calibration tube is made to flow into the gas separation columns.

5. A gas chromatographic apparatus, which comprises a gas calibration tube, a gas separation column connected to the gas calibration tube through a switch valve of switching a carrier gas passage, and a gas sensor connected to the gas separation column and destined to detect separated gas components, the gas separation column comprising a first gas separation column whose inlet is connected to the switch valve, and at least two second columns whose inlets are connected to the outlet of the first gas separation column, whose outlets are connected to the gas sensor, and which are arranged in parallel to each other through a column switch valve, one of said at least two second columns comprising pressure and flow rate-controlling means, where the first gas separation column, one of the second columns and the gas sensor are communicated with one another by the column switch valve.

6. The gas chromatographic apparatus according to claim 5, wherein both of the second columns arranged in parallel have an identical length, an identical inner diameter and fillers of identical particle size therein.

7. The gas chromatographic apparatus according to claim 5, wherein the column switch valve is a 3-way electromagnetic valve.

8. The gas chromatographic apparatus according to claim 1, wherein the gas detection time-controlling pipe has a length sufficient to permit the gas components separated in the second gas separation column to be detected by said gas sensor successively after completion to detect the gas components separated in the first gas separation column.

9. A gas chromatographic apparatus which comprises a gas calibration tube; a gas separation column connected to the gas calibration tube through a switch valve of switching a carrier gas passage; and a gas sensor connected to the gas separation column and destined to detect separated gas components; the gas separation column comprising at least two gas separation column means, each having a gas separation column, arranged in parallel to each other, the outlet of a first of said at least two gas separation column means being connected to the gas sensor through a column switch valve, the outlet of a second of said at least two gas separation column means being connected to the gas sensor through the column switch valve, with the column switch valve acting to prevent gas flow to the sensor from the second gas separation column means when the column switch valve permits gas flow from the first gas separation column means to the sensor; and wherein the second gas separation column means includes a gas detection time-controlling pipe, whereby the gas components separated in the second gas separation column means can be detected successively after completion to detect the gas components separated in the first gas separation column means.

10. The gas chromatographic apparatus according to claim 9, wherein said gas detection time-controlling pipe is positioned just prior to the inlet of the gas separation column of the second gas separation column means.

11. The gas chromatographic apparatus according to claim 9, wherein said gas detection time-controlling pipe is positioned just after the outlet of the gas separation column of the second gas separation column means.

12. The gas chromatographic apparatus according to claim 9, wherein said gas detection time-controlling pipe has an inner diameter of not more than 4 mm.

13. The gas chromatographic apparatus according to claim 6, wherein said one of said at least two second columns contains fillers having the same particle size as that of the other second columns but having no gas separability function.

14. The gas chromatographic apparatus according to claim 5, wherein said one of said at least two second columns contains fillers having the same particle size as that of the other second columns but having no gas separability function.

15. The gas chromatographic apparatus according to claim 5, wherein said one of said at least two second columns comprises auxiliary gas separation column means for further separating components separated in part in said first gas separation column.

16. The gas chromatographic apparatus according to claim 5, further comprising a gas detection time-controlling pipe positioned adjacent said one of said at least two second columns.

* * * * *